US009649496B2

United States Patent
Thakur et al.

(10) Patent No.: US 9,649,496 B2
(45) Date of Patent: May 16, 2017

(54) PHYSIOLOGIC RESPONSE TO A THERAPY CHANGE USING A VENTRICULAR FILLING CHARACTERISTIC

(71) Applicant: Cardiac Pacemakers, Inc., St. Paul, MN (US)

(72) Inventors: Pramodsingh Hirasingh Thakur, Woodbury, MN (US); Ramesh Wariar, Blaine, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/494,099

(22) Filed: Sep. 23, 2014

(65) Prior Publication Data
US 2015/0157234 A1 Jun. 11, 2015

Related U.S. Application Data

(60) Provisional application No. 61/912,922, filed on Dec. 6, 2013.

(51) Int. Cl.
*A61N 1/36* (2006.01)
*A61N 1/365* (2006.01)
(Continued)

(52) U.S. Cl.
CPC ...... *A61N 1/36585* (2013.01); *A61B 5/02028* (2013.01); *A61B 5/0468* (2013.01);
(Continued)

(58) Field of Classification Search
None
See application file for complete search history.

(56) References Cited

U.S. PATENT DOCUMENTS

| 4,773,401 A | 9/1988 | Citak et al. |
| 6,076,015 A | 6/2000 | Hartley et al. |

(Continued)

OTHER PUBLICATIONS

Nishimura, R A, et al., "Mechanism of hemodynamic improvement by dual-chamber pacing for severe left ventricular dysfunction: An acute Doppler and catheterization hemodynamic study", Journal of the American College of Cardiology, 25(2), (Feb. 1995), 281-288.

(Continued)

*Primary Examiner* — Brian T Gedeon
*Assistant Examiner* — Ankit D Tejani
(74) *Attorney, Agent, or Firm* — Schwegman Lundberg & Woessner, P.A.

(57) ABSTRACT

A system includes a therapy control circuit, a therapy output circuit; and a physiologic interval sensing circuit configured to receive information about subject physiologic intervals. The therapy circuit is configured to determine a change in therapy that is provided by the therapy output circuit, determine that the change in therapy includes a change to a maximum interval of cardiac electrostimulation provided according to the therapy, detecting a change in a ventricular filling characteristic of the subject in response to the change in maximum interval of cardiac electrostimulation, determine an indication of a physiologic response of the subject to the therapy change using information about the change in the ventricular filling characteristic, and update the subject therapy provided by the therapy output circuit when the determined indication of the physiologic response to the therapy change indicates an increased likelihood of worsening health status of the subject.

20 Claims, 3 Drawing Sheets

(51) Int. Cl.
*A61B 7/00* (2006.01)
*A61B 5/02* (2006.01)
*A61B 5/0468* (2006.01)
*A61B 5/00* (2006.01)
*A61B 5/0456* (2006.01)

(52) U.S. Cl.
CPC .............. *A61B 5/4836* (2013.01); *A61B 7/00* (2013.01); *A61N 1/36521* (2013.01); *A61B 5/0456* (2013.01)

(56) References Cited

U.S. PATENT DOCUMENTS

| | | | |
|---|---|---|---|
| 7,082,328 B2 | 7/2006 | Funke | |
| 2008/0288030 A1* | 11/2008 | Zhang | A61B 5/4869 607/62 |
| 2010/0179608 A1* | 7/2010 | Limousin | A61N 1/3627 607/5 |
| 2010/0305649 A1* | 12/2010 | Maskara | A61N 1/36564 607/23 |
| 2012/0185011 A1* | 7/2012 | Cornelussen | A61N 1/36585 607/18 |
| 2012/0296228 A1* | 11/2012 | Zhang | A61B 5/0006 600/513 |
| 2013/0226258 A1 | 8/2013 | Maskara et al. | |

OTHER PUBLICATIONS

Waggoner, A. D, et al., "Improvements in left ventricular diastolic function after cardiac resynchronization therapy are coupled to response in systolic performance", J Am Coll Cardiol., 46(12), (Dec. 20, 2005), 2244-9.

\* cited by examiner

PHYSIOLOGIC RESPONSE TO A THERAPY CHANGE USING A VENTRICULAR FILLING CHARACTERISTIC

CLAIM OF PRIORITY

This application claims the benefit of priority under 35 U.S.C. §119(e) of U.S. Provisional Patent Application Ser. No. 61/912,922, filed on Dec. 6, 2013, which is herein incorporated by reference in its entirety.

BACKGROUND

Ambulatory medical devices include implantable medical devices (IMDs) and wearable medical devices. Some examples of IMDs include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of IMDs include implantable diagnostic devices, implantable drug delivery systems, or implantable devices with neural stimulation capability.

Some examples of wearable medical devices include wearable cardioverter defibrillators (WCDs) and wearable diagnostic devices (e.g., an ambulatory monitoring vest). WCDs can he monitoring devices that include surface electrodes. The surface electrodes may be arranged to provide one or both of monitoring to provide surface electrocardiograms (ECGs) and delivery of cardioverter and defibrillator shock therapy. A wearable medical device can also include a monitoring patch worn by the patient such as an adherable patch or a patch included with an article of clothing worn by the patient.

Therapy provided by ambulatory medical devices is typically optimized by a caregiver in a clinical setting, such as by programming the medical device for example. Sometimes, the device may not be reprogrammed at all and the therapy is left at the original settings. The inventors have recognized a need for improved optimization of device-based therapy.

OVERVIEW

As explained previously herein, therapy provided by ambulatory medical devices is typically optimized by a caregiver in a clinical setting. The caregiver may look for changes in the hemodynamic status of the patient as a result of changing one or more therapy parameters while in the clinical setting. Because of the timeframe involved with the clinical visit, the therapy provided by medical device is typically optimized using observed changes that are acute, or changes that happen in a matter of seconds or minutes, or possibly hours if time permits. The present inventors have recognized that some changes may take place outside a clinical setting. For instance, some changes may occur over a timeframe that is more chronic in nature than acute (e.g., over days or weeks rather than minutes). It can be impractical to monitor for chronic changes while in a clinic. Also, as ambulatory medical devices become more complex, a therapy change may be initiated by the device itself or by a device communicating remotely with the ambulatory medical device. Changes in the hemodynamic status of the patient due to these types of changes may not be observable by the clinician. The present subject matter can help improve monitoring of the hemodynamic function of the patient to determine changes due to therapy adjustments, such as by using a medical device to monitor the hemodynamic function of the patient in response to a therapy adjustment.

A system example of the present subject matter includes a therapy control circuit, a therapy output circuit; and a physiologic interval sensing circuit configured to receive information about subject physiologic intervals. The therapy circuit may be configured to determine a change in therapy that is provided by the therapy output circuit, determine that the change in therapy includes a change to a maximum interval of cardiac electrostimulation provided according to the therapy, detect a change in a ventricular filling characteristic of the subject in response to the change in maximum interval of cardiac electrostimulation, determine an indication of a physiologic response of the subject to the therapy change using information about the change in the ventricular filling characteristic, and update the subject therapy provided by the therapy output circuit when the determined indication of the physiologic response to the therapy change indicates an increased likelihood of worsening health status of the subject.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
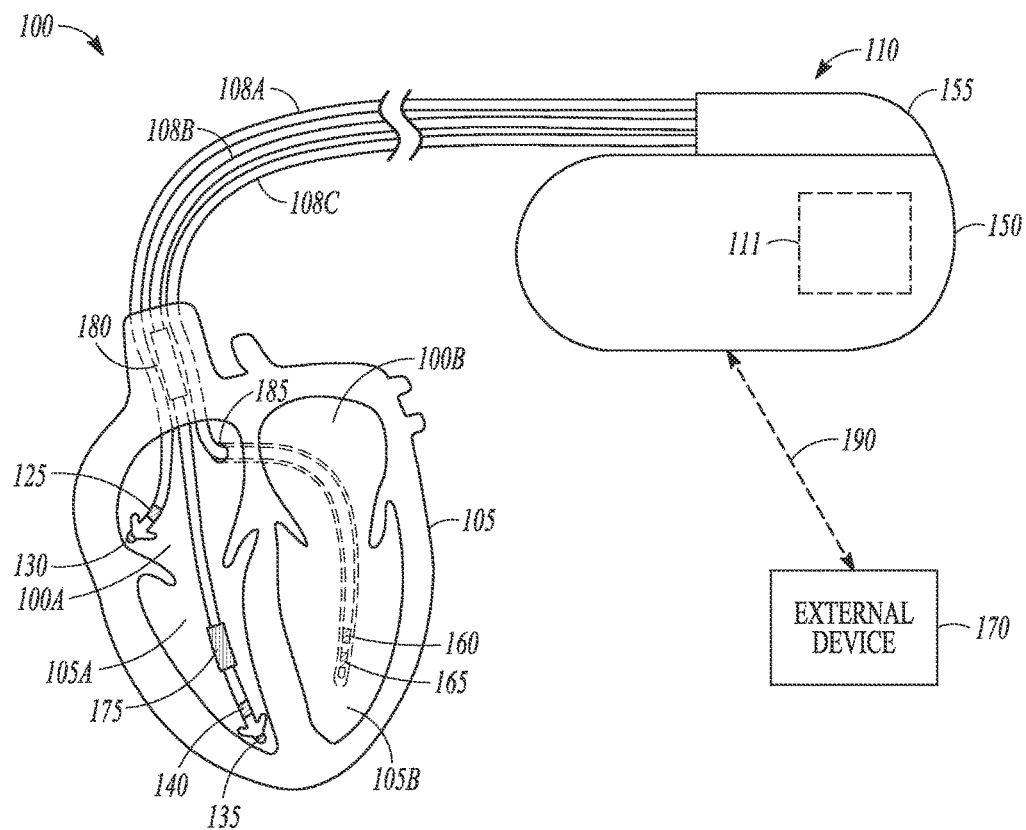
FIG. 1 is an illustration of portions of a medical device system that includes an ambulatory medical device that is an IMD.

FIG. 1 is an illustration of portions of a medical device system 100 that includes an ambulatory medical device that is an IMD 110. Examples of IMD 110 include, without limitation, a pacer, a defibrillator, a CRT device, or a combination of such devices. The system 100 also typically includes an external device 170 that may be an IMD programmer or other external device to communicate wireless signals 190 with the IMD 110, such as by using radio frequency (RF) or other telemetry signals.

The IMD 110 is shown coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120. Although only two electrodes are shown in the example of the Figure, lead 108C may include three electrodes, four electrodes, or any number of electrodes as desired.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed RID housing or can 150. This improves defibrillation by delivering current from the RV coil 175 more uniformly over the ventricular myocardium. In some examples, the therapy is delivered from the RV coil 175 only to the electrode formed on the MD can 150. In some examples, the coil electrodes 175, 180 are used in combination with other electrodes for sensing signals.

Note that although a specific arrangement of leads and electrodes are shown in the illustration, an IMD may be configured with a variety of electrode arrangements, including intrathoracic electrodes (e.g., transvenous, endocardial, and epicardial electrodes), non-intrathoracic electrodes (e.g., subcutaneous, can, header, and indifferent electrodes, subcutaneous array or lead electrodes), and electrodes for leadless devices that may be incorporated into a housing of the medical device. The present methods and systems will work in a variety of configurations and with a variety of electrodes.

The IMD can also include a physiologic sensor 111 that may not be coupled to electrodes. A physiologic sensor generates a physiologic signal that includes physiologic information of the subject. An example of a physiologic sensor is a heart sound sensing circuit. Heart sounds are associated with mechanical cardiac activity. This is in contrast to electrical cardiac activity that is associated with electrical action potentials due to cardiac depolarization. A "heart sound" can include a first heart sound (S1), a second heart sound (S2), a third heart sound (S3), a fourth heart sound (S4), or any components thereof, such as the aortic component of S2 (A2), the pulmonary component of S2 (P2), or other broadband sounds or vibrations associated with mechanical activity of the heart, such as valve closures or fluid movement (e.g., a heart. murmur, etc.). Heart sounds can also include one or more broadband chest sounds, such as may result from one or more of mitral regurgitation, left ventricle dilation, etc.

A heart sound sensing circuit may be configured to produce a sensed heart sound signal that is representative of at least one heart sound associated with mechanical cardiac activity of a subject. Some examples of a heart sound signal sensing circuit can include an accelerometer, a microphone, or other suitable heart sound sensing circuit.

Figure 2:
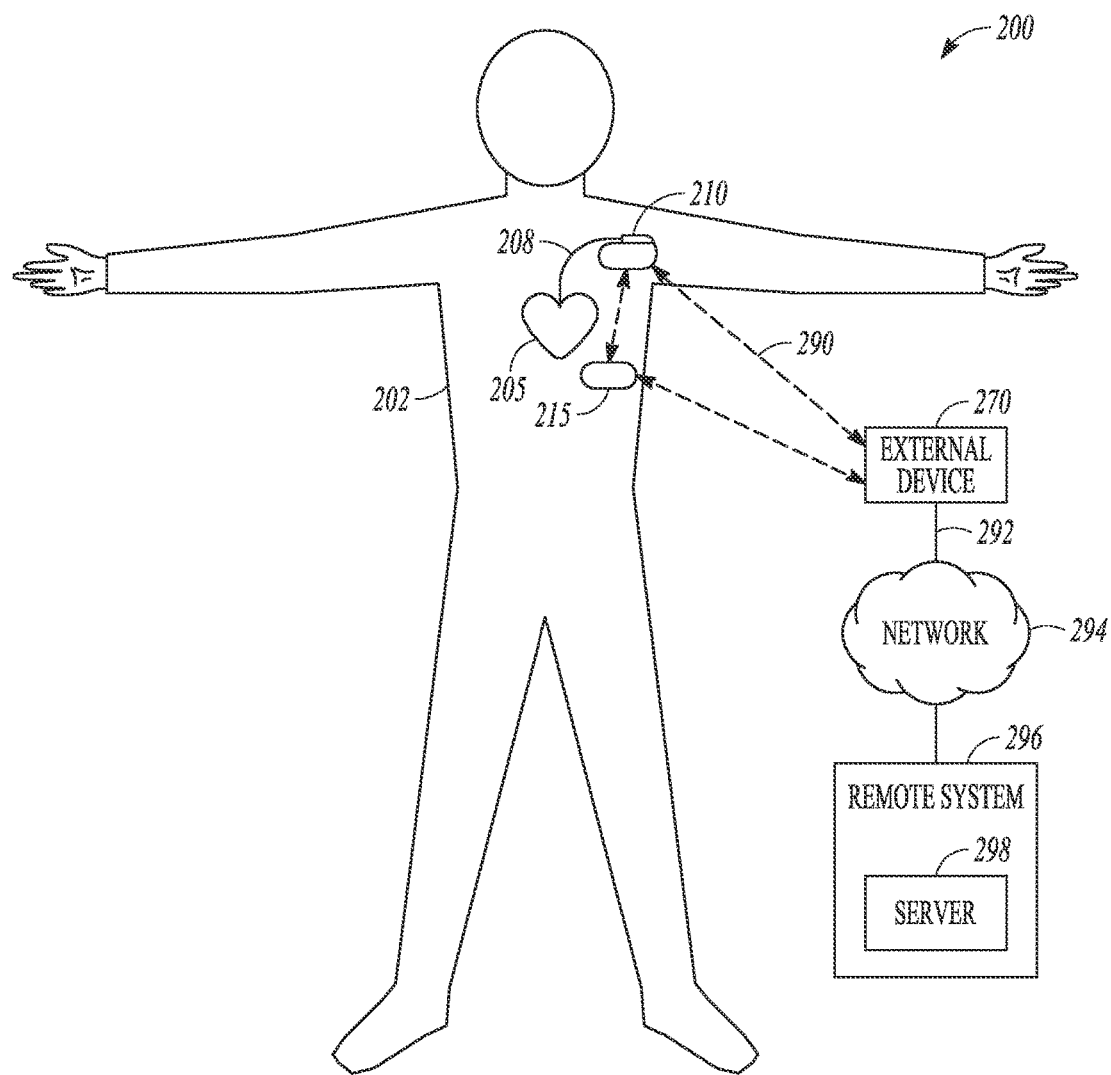
FIG. 2 is an illustration of portions of another medical device system that includes one or more ambulatory medical devices.

FIG. 2 is an illustration of portions of another medical device system 200 that includes one or more ambulatory medical devices. The one or more ambulatory medical devices can include an IMD 210 and a wearable medical device 215. The IMD 210 may provide a therapy to a patient 202 using implantable lead 208. The wearable medical device 215 may be a patch device that monitors one or more physiological parameters of the subject. The wearable medical device 205 may be incorporated into an article of clothing or may be temporarily adherable to the subject's skin.

The system 200 can include an external device 270 that communicates with a remote system 296 via a network 294. The network 294 can be a communication network such as a phone network or a computer network (e.g., the internet). In some examples, the external device 270 includes a repeater and communicates via the network using a link 292 that may be wired or wireless. In some examples, the remote system 296 provides patient management functions and may include one or more servers 298 to perform the functions. In certain examples, medical device system includes both the wearable medical device 215 and the IMD 210, and the wearable medical device 215 communicates with the IMD 210 using wireless signals 290.

As explained previously herein, adjusting the settings of an ambulatory medical device to optimize device-based therapy can benefit the subject by improving the subject's hemodynamic status. If device settings are changed by a caregiver, the resulting performance is typically only monitored over a relatively short timeframe while the subject is in a clinical setting. Also, some device settings may be changed automatically away from a clinical setting.

However, changing therapy parameters may produce changes that occur over a longer timeframe, and allowing an automatic change to a therapy parameter that appears to have low risk, may have unintended effects. For instance, the lower rate limit (LRL) of a pacemaker may be increased to improve cardiac output. The LRL is typically specified in beats per minute (bpm). The LRL interval is sometimes called a ventricular escape interval and is the time interval at the LRL. The LRL interval is typically specified in milliseconds (ms). An electrostimulation pulse is delivered to one or both of the ventricles to initiate contraction of the ventricles if an intrinsic ventricular depolarization is not detected by the time the escape interval times out. Alternatively, the LRL interval of a CFM device may be decreased in the presence of atrial tachyarrhythmia to counter a lack of a kick provided by the atrial chamber during a tachyarrhythmia such as atrial flutter. Yet decreasing the LRL interval may not increase cardiac output if the stroke volume is compromised by the increased ventricular contraction rate. If the time allowed for filling of the ventricles is inadequate, the left ventricle preload is inadequate and cardiac output will decrease. In the extreme case, decreasing the LRL interval to a point that cardiac output is inadequate can result in the subject experiencing syncope.

Figure 3:
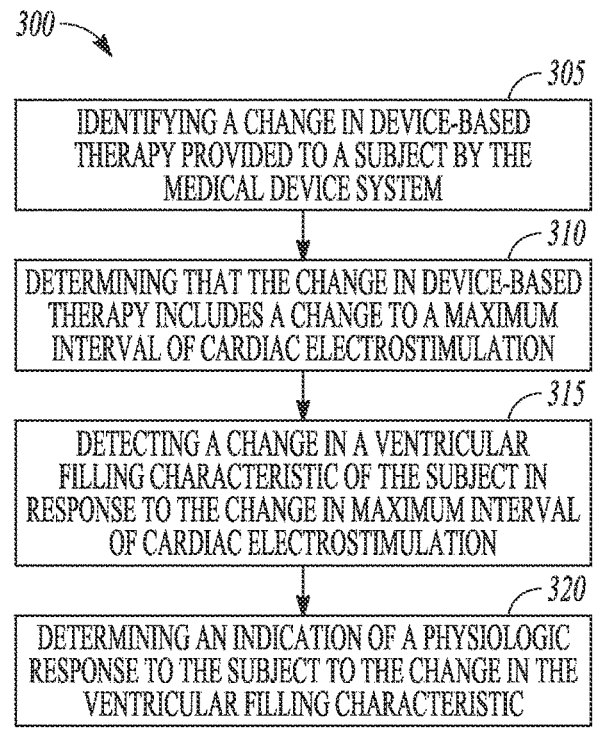
FIG. 3 is a flow diagram of an example of a method of operating a medical device system.

FIG. 3 is a flow diagram of an example of a method 300 of operating a medical device system. The method can be processor-implemented and may be performed by on one or more processors of the medical device system executing instructions to perform the functions described.

At block 305, a change is identified in device-based therapy provided to a subject by the medical device system. The therapy change may be identified by an ambulatory medical device of the system. The therapy change may originate with the ambulatory medical device itself as specified by the programming of the device, or the therapy change may be programmed into the ambulatory device by a second separate device.

At block 310, it is determined by the medical device system that the change in device-based therapy includes a change to a maximum interval of cardiac electrostimulation provided according to the device-based therapy. This determination may be made by determining that a register or memory location that holds a value of the maximum interval is being written or modified. In some examples, the change to a maximum interval of cardiac electrostimulation includes a decrease in an LRL interval.

At block 315, a change in a ventricular filling characteristic of the subject is detected in response to the change in the maximum interval of cardiac electrostimulation. The ventricular filling characteristic can include, among other things, at least a portion of a diastolic interval of the subject.

At block 320, an indication of a physiologic response of the subject to the change in the ventricular filling characteristic is determined. If the indication is that the subject is not responding well to the change, the medical device system may for example return the therapy to a previous setting and may generate an alert that an adverse indication was detected or otherwise identified. In some variations, the medical device system may set therapy parameters to default settings, or only generate the alert without changing therapy parameters.

According to some examples, the physiologic response of the subject includes an asymmetric change to the systolic interval and the diastolic interval of the subject. For instance, the change in the maximum interval of cardiac electrostimulation may result in a disproportionate shortening of the diastolic interval as compared to a shortening of the systolic interval. The asymmetric interval change may result in a low physiological tolerance of the subject to the change because of decreased filling of the ventricles. In some variations, an indication of a worsening subject health status is provided or generated when the change in the ventricular filling characteristic indicates decreased ventricular filling.

In some examples, the physiologic response of the subject to the change in the ventricular filling characteristic is determined indirectly without a direct or surrogate measurement of a ventricular filling characteristic. For instance, the medical device system may receive physiologic information of the subject from one or more physiologic sensors. Examples of such physiologic information include, among other things, information regarding sinus heart rate, stroke volume (e.g., cardiac end diastolic and end systolic volume), pulmonary/peripheral edema (e.g., interstitial edema, alveolar edema), thoracic fluid, intravascular volume or dimension (e.g., inferior vena cava or superior vena cava diameter), heart sounds (e.g., S1, S2, S3, S4), cardiac intervals (e.g., pre-ejection period, ejection time), cardiac filling pressure (e.g., left atrial pressure, right atrial pressure, right ventricular pressure, pulmonary artery pressure), and systemic blood pressure. The physiologic tolerance of the subject to the change in the ventricular filling characteristic can be determined using the hemodynamic information. One or more of a decrease in stroke volume, an increase in sinus rate, an increase in edema, a decrease in S1 magnitude, an increase in S3 magnitude, and an increase in cardiac filling pressure may indicate a low physiological tolerance of the subject to the change in therapy.

Figure 4:
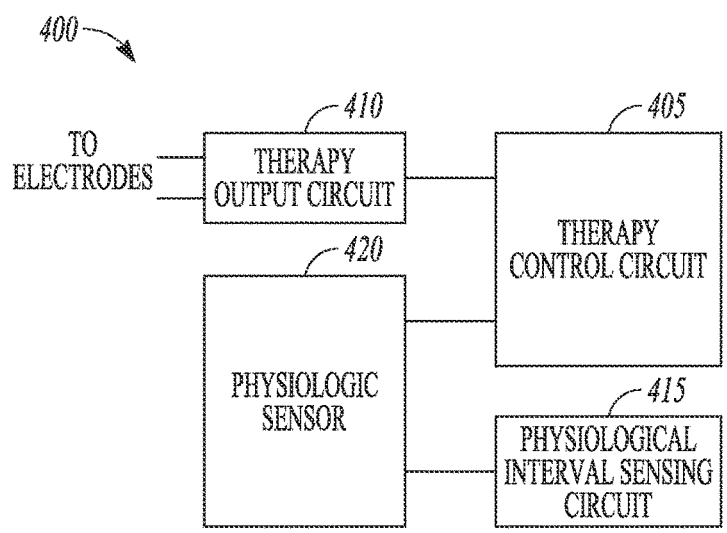
FIG. 4 is a block diagram of portions of an example of a medical device system.

FIG. 4 is a block diagram of portions of an example of a medical device system 400. The system can determine a physiologic response of a subject to a device-based therapy change. The system includes a therapy control circuit 405, a therapy output circuit 410, and a physiologic interval sensing circuit 415. The system can include an ambulatory medical device that includes the therapy control circuit 405, the therapy output circuit 410 and the physiologic interval sensing circuit 415. The physiologic sensor 420 may be included in the ambulatory medical device or may be included in a separate device (e.g., a wearable patch) and the physiological sensor signal can be communicated to the ambulatory medical device.

The therapy control circuit 405 can include a processor such as a microprocessor, a digital signal processor, application specific integrated circuit (ASIC), or other type of processor, interpreting or executing instructions in software modules or firmware modules. The modules may include software, firmware, hardware circuits or any combination of software, firmware, and hardware. Multiple functions can be performed in one or more of the modules as desired.

The therapy output circuit 410 can be coupled (e.g., electrically) to the therapy control circuit 405 and may generate a subject therapy. Examples of the therapy include electrical cardiac stimulation therapy such as one or more of pacing therapy, CRT, and anti-tachyarrhythmia pacing (ATP). The therapy output circuit can be electrically connectable to one or more therapy delivery electrodes, such as any of the electrodes described previously herein for example.

The physiologic interval sensing circuit 415 can be integral to the therapy control circuit 405 as a sub-circuit or module of the therapy control circuit 405, or can be separate from the therapy control circuit 405. The physiologic interval sensing circuit 415 receives information about subject physiologic intervals. The system can include a physiologic sensor 420 that provides a physiologic sensor signal and the physiologic interval sensing circuit 415 may receive information about the physiologic intervals of the subject using physiological sensor signal.

The therapy control circuit 405 can determine a change in the therapy that is provided or is to be provided by the therapy output circuit 410. The therapy change may be initiated by the therapy control circuit itself, or the therapy change can be communicated from a separate device such as a programmer or repeater. The therapy control circuit 405 determines whether the change in therapy includes a change to a maximum interval of cardiac electrostimulation (e.g., an LRL interval) provided according to the therapy.

When the therapy is changed, the therapy control circuit 405 can detect whether the change in the maximum interval produced a change to a ventricular filling characteristic of the subject. If such a change is produced, the system uses information about the ventricular filling characteristic to look for an indication of the physiologic response of the subject to the therapy change. In certain examples, the system enters a monitoring mode for a specified (e.g., programmed) period of time. The monitoring may be over a shorter timeframe (e.g., acute timeframe) or may be over a longer timeframe (e.g., a chronic timeframe).

If the indication is that the subject has a satisfactory physiologic response to the change in therapy (e.g., there is an increased likelihood that the health status of the subject improved), the system may do nothing when the monitoring timeframe expires and the therapy change stays as reprogrammed. If the indication is that the subject has an unsatisfactory or adverse physiologic response to the change in therapy (e.g., an indication of an increased likelihood that the health status of the subject worsened), the system may update the subject therapy provided by the therapy output circuit to correct the indication. For instance, if an increase in heart rate reduces a diastolic filing time, the system may return operation to a lower heart rate. In some examples, the medical device system may program the therapy to one or more default settings. In some examples, the medical device system generates an alert of an adverse physiological response. The alert may be to notify one or both of a patient and a caregiver. The alert may be generated local to the patient or remote form the patient such as by communicating the alert to a remote server. In certain examples, the alert is generated without changing a therapy parameter.

In certain examples, the indication of the physiological response is used by the therapy control circuit 405 to implement feedback control. If the information about the ventricular filling characteristic indicates that the diastolic filling interval may be too long, the therapy control circuit 405 may increase the heart rate of the subject. If the information about the ventricular filling characteristic indicates that the diastolic filling interval may be too short, the therapy control circuit 405 may decrease the heart rate of the subject.

The therapy change can be first implemented as a temporary change (e.g., a therapy algorithm may execute out of a portion of memory reserved for temporary operation). If the subject has a satisfactory physiologic response to the change in therapy, the therapy change is adopted after the monitoring timeframe expires (e.g., the therapy algorithm may be moved to a portion of memory reserved for normal operation). If the subject has an unsatisfactory physiologic response to the therapy change, the therapy control circuit 405 returns therapy operation back to the normal operation and the temporary operation is rejected.

In certain examples, if the indication is that the subject had an adverse physiologic response to the change in therapy, the therapy control circuit 405 may determine a likelihood of the subject experiencing a congestive heart failure (CHF) event using the determined indication of a physiologic response. The system may generate an alert based on the determined likelihood. The alert may include a message communicated to a separate device, or an indication readable by the separate device in a subsequent communication.

As explained previously, the therapy control circuit 405 can detect a change to a ventricular filling characteristic of the subject. According to some examples, the ventricular filling characteristic includes at least a portion of the diastolic interval of the subject. The change to the characteristic can be detected by measuring the diastole interval directly or by measuring a relative change to the diastole interval. The indication of the physiologic response can be generated based on the information about the diastolic interval. For instance, an indication of an adverse physiologic response can be generated by the therapy control circuit 405 when the information indicates that the diastolic interval does not allow adequate filling of the ventricles. In certain examples, the therapy control circuit 405 may require that the change to the diastolic interval be detected over multiple consecutive heartbeats before generating the indication of the physiologic response.

In some examples, the physiologic sensor 420 includes a heart sound sensing circuit that produces heart sound information. The S2 heart sound is associated with the beginning of diastole. A change in the diastolic interval can be detected by the physiological interval sensing circuit 415 identifying a change in the time interval between the S2 heart sound and the next S1 heart sound (an S2-S1 interval). The S2 heart sound can be identified in the heart sound signal by a fiducial feature representing the S2 heart sound and the S1 heart sound can be identified in the heart sound signal by a fiducial feature representing the S1 heart sound. The S2-S1 time interval is the time interval between the S2 and S1 fiducial features. If the S2-S1 time interval is less than a specified S2-S1 time interval, the diastolic time interval may be too short to provide adequate filling of the ventricles. Based on the measured S2-S1 time interval, the therapy control circuit 405 may generate an indication of an adverse physiologic response of the subject to the therapy change.

The specified S2-S1 time interval may be a threshold interval value, and the therapy control circuit 405 may generate the indication of an adverse physiologic response when the time interval is less than the threshold value. A threshold value to determine excessive shortening of the diastolic interval can be user-defined based on known filling times of the subject. A threshold value could also be determined statistically from a representative population that includes or represents the subject. In some variations, the threshold value could be predetermined based on distributions of diastolic filling times. Information regarding such distributions is readily available from echocardiographic studies. In some instance, the distribution (and the resultant thresholds) may be specified (e.g., programmed) by a caregiver based upon the values of patients at a clinic. The measure of the diastolic interval (e.g., S2-S1 interval) can be compared to multiple safety zones of threshold values. The indication of the physiological response is determined to be satisfactory if the measurement of the diastolic interval is greater than a $95^{th}$ percentile of the distribution (e.g., a green zone). The indication of the physiological response is determined to be unsatisfactory or adverse if the measurement of the diastolic interval is less than a $50^{th}$ percentile of the distribution (e.g., a red zone). A cautionary zone (e.g., a yellow zone) can be defined between the two zones. When an interval in the cautionary zone is detected, one or both of additional information can be obtained and the monitoring timeframe can be extended.

Sometimes, it may be difficult to determine an absolute threshold value for the comparison to the measured value. Comparing a change in the measured value relative to a change in a second interval may provide improvement in detection of a physiological response. In certain examples, the change in diastolic interval can be detected by identifying a change in the S2-S1 time interval relative to a change in an S1-S2 time interval, The two intervals can be determined from fiducial features in the heart sound signals that indicate the S1 and the S2 heart sounds. If the difference between S2-S1 time interval and S1-S2 time interval exceeds a specified difference value, this may indicate that the therapy change had a disproportionate effect on the diastolic filling time and the therapy control circuit 405 may generate an indication of an adverse physiologic response of the subject to the therapy change.

In some examples, the physiologic sensor circuit 420 further includes a cardiac signal sensor circuit that provides a cardiac signal representative of electrical heart activity of the subject. The physiological internal sensing circuit 415 may detect a fiducial feature in the cardiac signal representative of an R-wave of the QRS complex associated with ventricular depolarization. A change in the diastolic interval can be detected when the physiological interval sensing circuit 415 identifies a change in the time interval between an S2 heart sound and subsequent R-wave (an S2-R interval). If the S2-R time interval is less than a specified S2-R time interval, the diastolic time interval may be too short to provide adequate filling of the ventricles. Based on the measured S2-R interval, the therapy control circuit 405 may generate an indication of an adverse physiologic response of the subject to the therapy change.

In certain examples, the change in diastolic interval can be detected by identifying a change in the S2-R interval relative to a change in a time interval from an R-wave to R-wave interval (RR interval) of the subject. If the difference between S2-R time interval and R-R time interval is greater than a specified difference value, this may indicate that the S2-R time interval experienced a large change and the therapy change had a disproportionate effect on the diastolic filling time. Based on the change in the difference between the S2-R and R-R intervals, the therapy control circuit 405 may generate an indication of an adverse physiologic response of the subject to the therapy change. In certain examples, a ratio of the S2-R interval to the R-R interval is calculated by the therapy control circuit 405 and the therapy control circuit 405 may generate an indication of an adverse physiologic response when the ratio is less than a specified ratio value.

In some variations, the change in diastolic interval can be detected by identifying a change in the S2-R interval relative to a change in a time interval from an R-wave to an S1 heart sound (an R-S1 interval). The R-S1 interval and the S2-R interval can be monitored prior to making the therapy change and monitored after the therapy change, and a value of the difference between the R-S1 interval and the S2-R interval can be determined before and after the therapy change. If the interval difference value changes by more than a specified interval difference value, this may indicate that the diastolic interval may be too short to provide adequate filling of the ventricles. Based on the change in the difference between the S2-R and R-S1 intervals, the therapy control circuit 405 may generate an indication of an adverse physiologic response of the subject to the therapy change.

According to some examples, the ventricular filling characteristic may be determined using information provided by a physiologic sensor included in a device separate from the device that includes the therapy control circuit 405. In certain examples, the change in the ventricular filling characteristic may be identified using information about at least one diastolic filling parameter determined using echocardiography and provided to the therapy control circuit 405. For instance, the ventricular filling characteristic can be determined using information about one or both of an E-wave and an A-wave. An E-wave represents the peak mitral flow velocity during passive filling, and an A-wave represents the peak mitral flow velocity during atrial contraction. The information of one or both of an E-wave and A-wave can be used to detect a change in ventricular filling by identifying a change in blood flow during ventricular filling. In certain examples, the ventricular filling characteristic can be determined using a velocity time integral (VTI) determined using echocardiography. VTI can provide information of flow at the aortic valve during diastole.

The information obtained using echocardiography can be communicated to the therapy control circuit 405 from the separate device using wireless telemetry. The therapy control circuit 405 may use the information to determine a change in blood flow during diastolic filling after the therapy is changed, or the separate device may communicate values of blood flow to the therapy control circuit 405. If the determined value of blood flow is too small, the diastolic time interval may be too short to provide adequate filling of the ventricles. The therapy control circuit 405 may generate an indication of an adverse physiologic response due to the therapy change.

Instead of, or in addition to, measuring a ventricular filling characteristic, the physiological response of the subject may be deduced using one or both of information of hemodynamic status of the subject and information regarding fluid volume of the subject. Hemodynamic status information can be provided by a hemodynamic sensor and the information can include, among other things, information regarding blood flow, blood pressure, heart sounds, heart rate, respiratory rate, and intracardiac volumes. Fluid volume information can include information regarding interstitial fluid, intravascular fluid, thoracic fluid, and edema fluid. Fluid volume information can be deduced using sensors such as intrathoracic impedance or transthoracic impedance. Acute changes in weight of the subject can also be indicative of changes in fluid volume status of the subject. The therapy control circuit 405 receives the information regarding one or both of hemodynamic status and fluid volume, and determines an indication of physiological response using one or both of the information associated with the hemodynamic status and the information associated with fluid volume of the subject.

In certain examples, the physiologic sensor 420 includes a heart sound sensing circuit and the hemodynamic status information includes S1 amplitude information. A decrease in S1 amplitude may indicate a drop in contractility due to a reduced ventricular preload due to a shortened diastolic interval. The therapy control circuit 405 determines the indication of the physiologic response of the subject to the change in the ventricular filling characteristic includes using the received S1 amplitude information. The therapy control circuit may generate an indication of an adverse physiological response when the S1 amplitude is less than a specified S1 amplitude value.

In certain examples, the hemodynamic status information includes S3 amplitude information. An increase in S3 amplitude or the appearance of an S3 heart sound may indicate fluid back-up in the thoracic region due to inadequate preload of the ventricles (e.g., due to a shortened diastolic interval). The therapy control circuit 405 determines the indication of the physiologic response of the subject to the change in the ventricular filling characteristic using the received S3 amplitude information. The therapy control circuit may generate an indication of an adverse physiological response when the S3 amplitude is greater than a specified S3 amplitude value.

In certain examples, the physiologic sensor 420 includes a thoracic impedance sensor. The system may be electrically coupled to intrathoracic electrodes. A non-stimulating electrical pulse of a known current may be applied across the thorax region of the subject and a voltage resulting from the current can be measured across the thorax region. The thoracic impedance may then be determined using Ohm's Law. An approach to measuring thoracic impedance is described in Hartley et al., U.S. Pat. No. 6,076,015 "Rate Adaptive Cardiac Rhythm Management Device Using Transthoracic Impedance," filed Feb. 27, 1998, which is incorporated herein by reference in its entirety. Typically, the thoracic impedance signal includes the following components: a baseline or DC component that is indicative of fluid status, a respiratory component that is indication of lung volume changes within a respiratory cycle, and a cardiac component that is indicative of cardiac volume changes during a cardiac cycle. The respiratory component has a lower frequency than the cardiac component because the respiratory rate is typically less than the heart rate of the subject. Signal filtering allows the respiratory component to be extracted to enable measurements of lung volume.

Filtering also allows the cardiac component to be extracted to obtain the cardiac component of thoracic impedance information. The cardiac component of thoracic impedance information can be used as hemodynamic status information by the therapy control circuit 405. A decrease in cardiac thoracic impedance may indicate inadequate preloading of the ventricles. The therapy control circuit 405 determines the indication of the physiologic response of the subject to the change in the ventricular filling characteristic using the received cardiac thoracic impedance information. The therapy control circuit 405 may generate an indication of an adverse physiological response when the impedance is less than a specified impedance value.

In certain examples, the physiologic sensor 420 includes an intracardiac impedance impedance sensor. A non-stimulating electrical pulse of a known current may be applied across one or both ventricular chambers and the resulting voltage can be measured to determine intracardiac impedance. An example of a configuration that enables measurement of intracardiac impedance includes stimulation and sensing using LV and RV electrodes. Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety.

The hemodynamic status information received by the therapy control circuit 405 can include intracardiac impedance information. A decrease in intracardiac impedance prior to ventricular contraction may indicate inadequate preloading of the ventricles. The therapy control circuit 405 determines the indication of the physiologic response of the subject to the change in the ventricular filling characteristic using the received intracardiac impedance information.

In some examples, the physiologic sensor 420 includes an implantable pressure sensing circuit that generates cardiovascular pressure information. The information can be representative of at least one of arterial blood pressure, central venous pressure, coronary venous pressure, pulmonary artery pressure, and left atrial pressure of the subject. The therapy control circuit 405 may extract pressure information regarding one or more of arterial blood pressure, central venous pressure, pulmonary artery pressure, and left atrial pressure from the pressure signal. A decrease in the systemic or arterial blood pressure may indicate a shortened diastolic filling interval. On the other hand, an increase in left atrial pressure, pulmonary arterial pressure or central venous pressure may be indicative of fluid backup due to reduced ventricular pre-load. The therapy control circuit 405 determines the indication of the physiologic response of the subject to the change in the ventricular filling characteristic using the received cardiovascular pressure information. Other physiologic sensors that can provide hemodynamic status information include a heart rate sensor and a respiratory sensor.

In certain examples, the physiologic sensor 420 includes a fluid volume sensor. An example of a fluid volume sensor is a thoracic impedance sensor. As explained previously herein, a thoracic impedance signal can include a lower frequency lung component and a higher frequency cardiac component. The thoracic impedance signal can also include a very low or a near-zero frequency component. A decrease in this substantially DC component of the thoracic impedance of the subject may indicate a buildup of interstitial fluid in the subject. In some examples, the therapy control circuit receives weight information. An increase in weight of the subject in combination with other sensor information may indicate an increase in fluid volume of the subject.

One or both of hemodynamic status information and fluid volume information can be used to deduce a change in the ventricular filing characteristic or the information can be used in combination with one or measurements of the diastolic filling interval to identify a change in the ventricular filing characteristic. For instance, one or both of hemodynamic status information and fluid volume information can be used to help identify a change in the ventricular filing characteristic when a value of the diastolic interval is within a cautionary zone of a distribution of diastolic filling times as described previously.

As explained previously, the system may enter a monitoring mode for a specified period of time. Some physiological parameters are more suitable for monitoring during an acute timeframe. An example of such a physiological parameter includes intracardiac impedance, which may provide an indication of a change in cardiac volume. Some physiological parameters are more suitable for monitoring during a chronic timeframe, such as amplitude of the S3 heart sound and thoracic impedance because build up fluid may occur over a longer timeframe.

The methods, systems and device described herein provide advantages in monitoring the effects of device-based therapy. Because the monitoring is also device-based, changes in the health status of the patient due to therapy changes can be brought to the attention of the caregiver without the need for a visit by the patient to a clinic.

ADDITIONAL NOTES & EXAMPLES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples for one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of operating a medical device system, the method comprising:
   determining changes in device-based therapy provided to a subject using a therapy output circuit of the medical device system, wherein the therapy output circuit is coupleable to a therapy delivery electrode;
   identifying that the changes in device-based therapy include changes to a maximum interval of cardiac electrostimulation provided according to the device-based therapy;
   identifying increases and decreases in a diastolic filling interval of the subject resulting from the changes in maximum interval of cardiac electrostimulation;
   determining an indication of physiologic response of the subject to the increases and decreases in the diastolic filling interval, including determining a disproportionate change in a diastolic interval compared to a change in a corresponding systolic interval resulting from the changes in maximum interval of cardiac electrostimulation; and
   adjusting a therapy control circuit according to the determined indication of physiologic response.

2. The method of claim 1, wherein the determining the indication of the physiologic response of the subject to the increases and decreases in the diastolic filling interval includes receiving, by a medical device, physiologic information of the subject from a physiologic sensor, and determining a physiologic tolerance of the subject to the increases and decreases in the diastolic filling interval using the physiologic information.

3. The method of claim 2, wherein receiving physiologic information includes receiving information associated with hemodynamic status of the subject from the physiologic sensor, wherein the determining the indication of a physiologic response of the subject to the increases and decreases in the diastolic filling interval includes determining the indication using the information associated with the hemodynamic status.

4. The method of claim 3, wherein the receiving information associated with hemodynamic status of the subject includes receiving at least one of S1 amplitude information or S3 amplitude information from a heart sound sensing circuit, and wherein the determining the indication of the physiologic response of the subject to increases and decreases in the diastolic filling interval includes determining the indication using the at least one of the received S1 amplitude information or S3 amplitude information.

5. The method of claim 3, wherein the receiving information associated with hemodynamic status of the subject includes receiving intracardiac impedance information, and wherein the determining the indication of the physiologic response of the subject to the increases and decreases in the diastolic filling interval includes determining the indication using the received intracardiac impedance information.

6. The method of claim 2, wherein the receiving physiologic information includes receiving information associated with fluid volume of the subject, and wherein the determining the indication of the physiologic response of the subject to the increases and decreases in the diastolic filling interval includes determining the indication using received fluid volume information.

7. The method of claim 1, wherein the identifying increases and decreases in the diastolic filling interval of the subject includes identifying a change in at least a portion of a diastolic interval of the subject; and wherein the determining the indication of the physiologic response of the subject to the increases and decreases in the diastolic filling interval includes determining the indication using information of a change in the at least a portion of the diastolic interval and information of a specified diastolic interval characteristic.

8. The method of claim 7, wherein the identifying the change in at least a portion of the subject diastolic interval includes identifying a change in a time interval between an S2 heart sound and an R-wave (an S2-R interval).

9. The method of claim 8, wherein the identifying the change in at least a portion of the subject diastolic interval includes identifying a change in the S2-R interval relative to a change in a time interval from an R-wave to an S1 heart sound (an R-S1 interval).

10. The method of claim 7, wherein the identifying the change in at least a portion of the subject diastolic interval includes identifying a change in a time interval between an S2 heart sound and an Si heart sound (an S2-S1 interval).

11. The method of claim 10, wherein the identifying the change in at least a portion of the subject diastolic interval includes identifying a change in the S2-S1 time interval relative to a change in an S1-S2 time interval.

12. The method of claim 7, wherein the identifying the change in at least a portion of the subject diastolic interval includes identifying a change in the at least a portion of the diastolic interval relative to an R-wave to R-wave interval (R-R interval) of the subject.

13. The method of claim 1, wherein the identifying that the change in device-based therapy includes a change to a maximum interval of cardiac electrostimulation includes identifying that the change includes a change in the lower rate limit (LRL interval.

14. The method of claim 1, wherein the determining the indication of the physiologic response of the subject to the therapy change includes providing an indication of a worsening subject health status when the change in the ventricular filling characteristic indicates decreased ventricular filling.

15. A system comprising:
 a therapy control circuit;
 a therapy output circuit coupled to the therapy control circuit and configured to generate a subject therapy, the therapy output circuit coupleable to a therapy delivery electrode; and
 a physiologic interval sensing circuit configured to receive information about subject physiologic intervals;
 wherein the therapy control circuit is configured to:
 determine changes in therapy that include changes to a maximum interval of cardiac electrostimulation provided according to the therapy;
 detect increases and decreases in a diastolic filling interval of the subject resulting from the changes in maximum interval of cardiac electrostimulation;
 determine an indication of a physiologic response of the subject to the increases and decreases in the diastolic filling interval, including determine a disproportionate change in a diastolic interval compared to a change in a corresponding systolic interval resulting from the changes in maximum interval of cardiac electrostimulation; and
 update the subject therapy provided by the therapy output circuit when the determined indication of the physiologic response to the therapy change indicates an increased likelihood of worsening health status of the subject.

16. The system of claim 15, wherein the therapy control circuit is configured to update the subject therapy provided by the therapy output circuit when the increases and decreases in the diastolic filling interval of the subject indicates decreased ventricular filling.

17. The system of claim 15, wherein the physiologic interval sensing circuit is configured to receive subject diastolic interval information, and wherein the therapy control circuit is configured to identify increases and decreases in the diastolic filling interval of the subject using the received subject diastolic interval information.

18. The system of claim 17, comprising at least one of a hemodynamic sensor or fluid volume sensor, wherein the therapy control circuit is configured to update the therapy provided by the therapy output circuit when information from the at least one of the hemodynamic sensor or fluid volume sensor indicates a change in cardiac contractility and the determined indication of the physiologic response of the subject to the therapy change indicates an increased likelihood of the subject experiencing a CHF event.

19. The system of claim 17, comprising a fluid volume sensor, wherein the therapy control circuit is configured to update the therapy provided by the therapy output circuit when information from the fluid volume sensor indicates a change in thoracic impedance and the determined indication of the physiologic response of the subject to the therapy change indicates an increased likelihood of the subject experiencing a CHF event.

20. A processor-implemented method to execute on one or more processors, the method comprising:
 identifying a change in an electrostimulation lower rate limit used by an ambulatory medical device to provide a cardiac pacing therapy to a subject;
 identifying a change in a diastolic interval of the subject in response to the change in the electrostimulation lower rate limit; and
 determining a likelihood of the subject experiencing a congestive heart failure (CHF) event using information of the change in the diastolic interval and information about a specified diastolic interval characteristic, wherein the information about the diastolic interval of the subject is determined at least in part using information from a heart sound sensing circuit, including determine a disproportionate change in a diastolic interval compared to a change in a corresponding systolic interval resulting from the change in electrostimulation lower rate limit.

* * * * *